(12) United States Patent
Fuladi

(10) Patent No.: US 11,058,651 B2
(45) Date of Patent: Jul. 13, 2021

(54) TOPICAL COMPOSITION FOR PAIN RELIEF

(71) Applicant: Bob Fuladi, Santa Barbara, CA (US)

(72) Inventor: Bob Fuladi, Santa Barbara, CA (US)

(*) Notice: Subject to any disclaimer, the term of this patent is extended or adjusted under 35 U.S.C. 154(b) by 33 days.

(21) Appl. No.: 16/708,608

(22) Filed: Dec. 10, 2019

(65) Prior Publication Data
US 2020/0163910 A1 May 28, 2020

Related U.S. Application Data

(63) Continuation-in-part of application No. 16/009,067, filed on Jun. 14, 2018, now Pat. No. 10,517,821.

(51) Int. Cl.
| | |
|---|---|
| A61K 36/00 | (2006.01) |
| A61K 31/167 | (2006.01) |
| A61P 29/00 | (2006.01) |
| A61K 31/10 | (2006.01) |
| A61K 36/28 | (2006.01) |
| A61K 31/125 | (2006.01) |
| A61K 36/185 | (2006.01) |
| A61K 36/752 | (2006.01) |
| A61K 36/886 | (2006.01) |
| A61K 35/57 | (2015.01) |
| A61K 31/045 | (2006.01) |
| A61K 31/12 | (2006.01) |
| A61K 36/67 | (2006.01) |
| A61K 9/00 | (2006.01) |
| A61K 9/06 | (2006.01) |
| A61K 31/60 | (2006.01) |

(52) U.S. Cl.
CPC .......... *A61K 31/167* (2013.01); *A61K 9/0014* (2013.01); *A61K 9/06* (2013.01); *A61K 31/045* (2013.01); *A61K 31/10* (2013.01); *A61K 31/12* (2013.01); *A61K 31/125* (2013.01); *A61K 31/60* (2013.01); *A61K 35/57* (2013.01); *A61K 36/185* (2013.01); *A61K 36/28* (2013.01); *A61K 36/67* (2013.01); *A61K 36/752* (2013.01); *A61K 36/886* (2013.01); *A61P 29/00* (2018.01)

(58) Field of Classification Search
CPC ..................................................... A61K 36/00
See application file for complete search history.

(56) References Cited

U.S. PATENT DOCUMENTS

| | | | |
|---|---|---|---|
| 6,579,543 B1 | 6/2003 | McClung | |
| 8,337,869 B2 | 12/2012 | Gross | |
| 9,095,563 B2 | 8/2015 | Sekura et al. | |
| 2003/0180347 A1* | 9/2003 | Young | A61K 8/0208 424/449 |
| 2006/0194759 A1 | 8/2006 | Eidelson | |

FOREIGN PATENT DOCUMENTS

JP          2010070501 A          4/2010

* cited by examiner

*Primary Examiner* — Michael V Meller
(74) *Attorney, Agent, or Firm* — Ocean Law; Paul D. Chancellor

(57) ABSTRACT

A topical composition for nociceptive and neuropathic pain relief comprising one or more of menthol, camphor, methyl sulfonyl methane, lidocaine, *Arinica montana*, harpagophytum tincture, Emu oil, maqui powder, turmeric oil and in some embodiments methyl salicylate or capsaicin with *Cannabis sativa*.

1 Claim, 3 Drawing Sheets

| Item | Ingredient | Weight Percent (%) |
|---|---|---|
| 1 | Methyl Salicylate | 15 |
| 2 | Menthol | 8 |
| 3 | Camphor | 3 |
| 4 | MSM | 5 |
| 5 | Lidocaine | 2 |
| 6 | Arnica Montana | 5 |
| 7 | Devil Extract (Harpagophytum tincture) | |
| 8 | Emu Oil | |
| 9 | Maqui Powder | |
| 10 | Curcumin extract or Curcuma Longa (Tumeric) oil or curcumin aromatica or curcumin aromatica non-staining | |

| Item | Ingredient | Weight Percent (%) |
|---|---|---|
| 1 | Capsaicin extract | 0.28 |
| 2 | Cannabis Sativa (Hemp) oil | |
| 3 | Menthol | 8 |
| 4 | Camphor | 3 |
| 5 | MSM | |
| 6 | Lidocaine | 2 |
| 7 | Arnica Montana | 5 |
| 8 | Devil Extract (Harpagophytum tincture) | |
| 9 | Emu Oil | |
| 10 | Maqui Powder | |
| 11 | Curcumin extract or Curcuma Longa (Tumeric) oil or curcumin aromatica or curcumin aromatica non-staining | |

FIG. 3

| Ingredient | Purpose |
|---|---|
| Aloe Vera | anti-inflammatory/skin permeation and repair |
| Arnica Montana (Flower extract) obtained from 5% w/w of raw material* | analgesic |
| Bergamot oil | analgesic/relaxant/improved circulation |
| Camphor | analgesic/anti-itch/counterirritant |
| Cannabis Sativa (Hemp) oil | analgesic/anti-inflammatory |
| Capsaicin extract obtained from 0.75% raw material | analgesic |
| Curcumin extract or Curcuma Longa (Tumeric) oil or curcumin aromatica or curcumin aromatica non-staining | anti-inflammatory/antioxidant/analgesic |
| Emu Oil | anti-inflammatory/skin moisturizer |
| Ginger extract obtained from 1%w/w of raw Ginger* | anti-inflammatory/antioxidant |
| Harpagophytum tincture (Devil extract) obtained from 2.5% w/w of raw material* | analgesic/anti-inflammatory |
| Lidocaine | local anesthesia |
| Maqui powder* | potent antioxidant |
| Menthol | local anesthetic, analgesic |
| Methyl Salicylate | counterirritant/analgesic |
| MSM (Methyl sulfonyl methane) | anti-inflammatory, skin permeation and repair |
| Piper nigrum (Black pepper) oil | enhancement of curcumin bioavailability, anti-inflammatory |

US 11,058,651 B2

TOPICAL COMPOSITION FOR PAIN RELIEF

PRIORITY CLAIM

This application is a continuation-in-part of U.S. patent application Ser. No. 16/009,067 filed Jun. 14, 2018 and entitled Topical Composition For Pain Relief.

BACKGROUND OF THE INVENTION

Many people suffer from pains including musculoskeletal conditions such as soft tissue trauma and arthritis. Some bear the pain associated with those conditions for prolonged periods. Treatment of musculoskeletal pain using traditional analgesics and anti-inflammatory drugs and known combinations of traditional analgesics anti-inflammatory drugs is not always effective.

Field of Invention

This invention relates to the medicinallchemical arts and to the treatment of nociceptive and neuropathic pain in humans.

Discussion of the Related Art

Medications for the relief of pain may include analgesics and anti-inflammatories. However, compositions that include these ingredients along with local anesthetics and/or counterirritants are not well known.

SUMMARY OF THE INVENTION

The present invention provides a composition or topical cream useful for treating nociceptive and neuropathic pain in humans.

In an embodiment, a composition includes by weight percent about 15% of counterirritant/analgesic methyl salicylate, 8% of anesthetic/analgesic, 5% of skin permeator/anti-inflammatory, 3.0% of analgesic/anti-itch/counterirritant, 2.9% of analgesic, 2.5% of analgesic/anti-inflammatory, 2.0% of anesthetic, 1.5% of antioxidant. In various embodiments, the ingredients of this composition are varied in a range of plus or minus 50%; for example, the anesthetic/analgesic is varied from 4% to 12%. In various embodiments, the ingredients of this composition are varied in a range of plus or minus 40%, in a range of plus or minus 30%, in a range of plus or minus 20%, in a range of plus or minus 10%, in a range of plus or minus 5%.

In an embodiment, a composition includes by weight percent about 8% of anesthetic/analgesic menthol, 5% of anti-inflammatory/skin permeator, 3.19% of analgesic, 3% of analgesic/anti-itch/counterirritant, 2.625% of analgesic/anti-inflammatory, 2% of anesthetic, 1.5% of antioxidant. In various embodiments, the ingredients of this composition are varied in a range of plus or minus 50%; for example, the anesthetic/analgesic ingredient is varied from 4% to 12%. In various embodiments, the ingredients of this composition are varied in a range of plus or minus 40%, in a range of plus or minus 30%, in a range of plus or minus 20%, in a range of plus or minus 10%, in a range of plus or minus 5%.

In an embodiment, a composition includes therapeutically effective amounts of methyl salicylate, methyl sulfonyl methane, *Arnica montana*, camphor, harpagophytum tincture, lidocaine, and maqui. The composition may further include any of aspirin, bergamot oil or capaiba oil, natural saffron yellow or clear white color formula, stearic acid, cetyl alcohol, isopropyl palmitate, propyl paraben, sorbitan monostearate, methyl paraben, sorbitol solution, polysorbate 60, and purified water.

In an embodiment, a composition includes therapeutically effective amounts of acetyl salicylate, methyl sulfonyl methane, lidocaine, *Arnica montana*, ginger extract, non-staining clear curcumin extract, harpagophytum tincture, menthol, camphor, maqui powder, emu oil, and aloe vera. The composition may further include any of bergamot oil or capaiba oil, natural saffron yellow or clear white color formula, stearic acid, cetyl alcohol, isopropyl palmitate, propyl paraben, sorbitan monostearate, methyl paraben, sorbitol solution, polysorbate 60, and purified water.

In an embodiment, a composition includes therapeutically effective amounts of capsaicin extract, methyl sulfonyl methane, lidocaine, *Arnica montana*, ginger extract, harpagophytum tincture, menthol, camphor, maqui powder, emu oil, aloe vera, *Piper nigrum* oil, *Curcuma longa* oil or non-staining clear curcumin extract, and *Cannabis sativa* oil. The composition may further include any of bergamot oil or capaiba oil, natural saffron yellow color or clear white color formula, stearic acid, cetyl alcohol, isopropyl palmitate, propyl paraben, sorbitan monostearate, methyl paraben, sorbitol solution, polysorbate 60, cabopol 940, and purified water.

BRIEF DESCRIPTION OF THE DRAWINGS

The present invention is described with reference to the accompanying figures. These figures, incorporated herein and forming part of the specification, illustrate the present invention and, together with the description, further serve to explain the principles of the invention and to enable a person skilled in the relevant art to make and use the invention.

FIG. 1 shows an embodiment of the invention wherein methyl salicylate is a main ingredient.

FIG. 2 shows an embodiment of the invention where capsaicin and hemp oil are ingredients used in place of methyl salicylate.

FIG. 3 shows the purpose of the ingredients used in the invention.

DETAILED DESCRIPTION OF THE PREFERRED EMBODIMENTS

The disclosure provided in the following pages describes examples of some embodiments of the invention. The designs, figures, and descriptions are non-limiting examples of certain embodiments of the invention. For example, other embodiments of the disclosed device may or may not include the features described herein. Moreover, disclosed advantages and benefits may apply to only certain embodiments of the invention and should not be used to limit the disclosed inventions.

In an embodiment, the invention comprises the ingredients shown in Table 1 below.

TABLE 1

Topical Composition For Pain Relief
Ingredients In A First Embodiment

| Item | Ingredients | Supplier (Lot number) + other information | % W/W | ASA-150 gm batch (gm) |
|---|---|---|---|---|
| 1 | Acetyl or Methyl Salicylate | Spectrum | 15.00 | 22.5 |
| 2 | MSM (Methyl sulfonyl methane) | Source Naturals (SN1535 REVK151) used by May 2020 | 5.00 | 7.5 |
| 3 | Lidocaine | Spectrum USP (IEC0028) Re test date Jun. 17, 2019 | 2.00 | 3.0 |
| 4 | Arnica Montana (Flower extract) obtained from 5% w/w of raw material (extracted amount along with propylene glycol for 150 gm of batch (gm)) | TerraVita (512592) Best Before April 2022 | 2.91 | 4.4 |
| 5 | Ginger extract obtained from 1% w/w of raw Ginger (extracted amount along with propylene glycol for 150 gm of batch (gm)) | Starwest Botanical (68499) | 0.50 | 0.8 |
| 6 | Harpagophytum tincture (Devils claw extract) | Bulk Supplements.com | 2.50 | 3.8 |
| 7 | Menthol | Spectrum (1EE0771) Exp. Date: Apr. 13, 2018 | 8.00 | 12.0 |
| 8 | Camphor | Spectrum (2EC0027) Exp. Date: Sep. 30, 2019 | 3.00 | 4.5 |
| 9 | Maqui powder extract (extracted amount along with propylene glycol for 150 gm of batch (gm)) | South Life (MFDP2016-08) Packing date Feb. 29, 2016 | 1.53 | 2.3 |
| 10 | Emu Oil | PipingRock.com (6250) Exp. Date: not available | 0.20 | 0.3 |
| 11 | Aloe Vera | Bulk Supplements.com (12E0916) Best before Sep. 15, 2020 | 1.00 | 1.5 |
| 12 | Piper nigrum (Black pepper) oil | Eden gardern | 0.08 | 0.1 |
| 13 | Curcumin extract or Curcuma Longa (Tumeric) oil or curcumin aromatica or curcumin aromatica non-staining | Eden gardern | 0.13 | 0.2 |
| 14 | Bergamot or Copaiba oil | Dr Adorable Inc, Exp. Date December 2018 | 0.30 | 0.5 |
| 15 | Natural Saffron yellow color Formula 3635C or light pink or beige color formula | Color Maker (Mfg. date Jun. 21, 2017) | 0.20 | 0.3 |
| 16 | Cream Base | | 56.66 | 86.49 |
| | TOTALS | | 100 | 150 |

The cream base referred to in Table 1 is shown in Table 2 below.

TABLE 2

Cream Base

| Item | Ingredients | Supplier (Lot number) + other information | % W/W | ASA-150 gm batch (gm) |
|---|---|---|---|---|
| 1 | Stearic acid | Spectrum NF (2FF0167) | 16.00 | 24.0 |
| 2 | Cetyl Alcohol | USB (36653-82-4) | 1.00 | 1.5 |
| 3 | Isopropyl Palmitate | Spectrum NF (2F10111) | 1.00 | 1.5 |
| 4 | Propyl Paraben | VWR USP (1GA0299) | 0.15 | 0.2 |
| 5 | Sorbitan Monostearate | Spectrum NF (2FG0337) | 5.00 | 7.5 |
| 6 | Methyl Paraben | VWR (3197C372) | 0.10 | 0.2 |
| 7 | Sorbitol Solution (70%) | Spectrum USP (1GC1050) | 3.00 | 4.5 |
| 8 | Polysorbate 60 | Spectrum NF (L-15031-AP) | 5.00 | 7.5 |
| 9 | Cabopol 940 | Lutriol | 0.25 | 0.4 |
| 10 | Purified water q.s. | In House | 26.16 | 39.2 |
| | TOTALS | | 56.66 | 86.49 |

Manufacturing Procedure

In a first step, weigh specified amounts of MSM, emu oil, maqui powder extract, ginger extract, Arnica montana flower extract, devils claw extract, Aloe vera, methyl paraben, sorbitol solution, polysorbate 60, carbopol 940 and purified water in a suitable glass container and heat to 80±5° C. on a heated water bath and stir the mixture to disperse the mixture completely.

In a second step, weight and mix specified amounts of methyl salicylate, lidocaine, stearic acid, cetyl alcohol, isopropyl palmitate, propyl paraben, Piper nigrum (black pepper) oil, Curcuma longa (tumeric) oil, and sorbitan monostearate separately in a suitable glass container and heat to 80±5° C. on a heated water bath. Stir the dispersion to mix all components.

In a third step, mix the components of step-II with the components of step-I at 80±5° C. under continuous homogenization for 10-15 minutes.

In a fourth step, remove the mixture from the heated water bath, add specified amount of menthol, camphor, natural saffron yellow color formula 3635C and flavoring agent (bergamot mint oil) and stir continuously to disperse them uniformly.

In a fifth step, add the cream base.

In a sixth step, when the temperature of the composition is just above the solidification, the formulation is poured in to the suitable well labeled aluminum tubes. The final product is cooled down to room temperature, capped and stored at room temperature.

In an embodiment, the invention comprises the ingredients shown in Table 3 below.

TABLE 3

Topical Composition For Pain Relief
Ingredients In A Second Embodiment

| Item | Ingredients | Supplier (Lot number) + other information | % W/W | For 150 gm batch non-ASA (gm) |
|---|---|---|---|---|
| 1 | Capsaicin extract obtained from 0.75% raw material | Starwest Botanical (70519) Exp. Date: Jun. 20, 2019 | 0.28 | 0.4 |
| 2 | MSM (Methyl sulfonyl methane) | Source Naturals (SN1535 REVK151) used by May 2020 | 5 | 7.5 |
| 3 | Lidocaine | Spectrum USP (IEC0028) Re test date Jun. 17, 2019 | 2 | 3.0 |
| 4 | Arnica Montana (Flower extract) obtained from 5% w/w of raw material (extracted amount along with propylene glycol for 150 gm of batch (gm)) | TerraVita (512592) Best Before April 2022 | 2.91 | 4.4 |
| 5 | Ginger extract obtained from 1% w/w of raw Ginger (extracted amount along with propylene glycol for 150 gm of batch (gm)) | Starwest Botanical (68499) Exp. Date: Not available | 0.5 | 0.8 |
| 6 | Harpagophytum tincture (Devils claw extract) obtained from 2.5% w/w of raw material* | Bulk Supplements.com | 2.5 | 3.8 |
| 7 | Menthol | Spectrum (1EE0771) Exp. Date: Apr. 13, 2018 | 8 | 12.0 |
| 8 | Camphor | Spectrum (2EC0027) Exp. Date: Sep. 30, 2019 | 3 | 4.5 |
| 9 | Maqui powder extract (extracted amount along with propylene glycol for 150 gm of batch (gm)) | South Life (MFDP2016-08) Packing date Feb. 29, 2016 | 1.53 | 2.3 |
| 10 | Emu Oil | PipingRock.com (6250) Exp. Date: not available | 0.2 | 0.3 |
| 11 | Aloe Vera | Bulk Supplements.com (12E0916) Best before Sep. 15, 2020 | 1 | 1.5 |
| 12 | Piper nigrum (Black pepper) oil | Eden gardern | 0.075 | 0.1 |
| 13 | Curcumin Extract or Curcuma Longa (Tumeric) oil or curcumin aromatica or non-staining curcumin aromatica | Eden gardern | 0.125 | 0.2 |
| 14 | Cannabis Sativa (Hemp) oil | Eden gardern | 0.125 | 0.2 |
| 15 | Bergamot or Copaiba oil | Dr Adorable Inc, Exp. Date December 2018 | 0.3 | 0.5 |
| 16 | Natural Saffron yellow color Formula 3635C or light pink or beige color formula | Color Maker (Mfg. date Jun. 21, 2017) | 0.2 | 0.3 |
| 17 | Cream Base | | 75.535 | 113.28 |
| | TOTALS | | 100 | 150 |

The cream base referred to in Table 3 is shown in Table 2 above.

In some embodiments, the methyl salicylate listed in Table 1 is included in the list of ingredients shown in Table 3 with or without the capsaicin extract. The weight percent of this additional ingredient may be 15% with the cream base reduced by a corresponding amount. If the capsaicin extract is excluded, the cream base may be increased by a corresponding amount.

Manufacturing Procedure

In a first step, weigh specified amounts of MSM, emu oil, maqui powder extract, ginger extract, *Arnica montana* Flower extract, devils claw extract, aloe vera, methyl paraben, sorbitol solution, polysorbate 60, carbopol 940 and purified water in a suitable glass container and heat to 80±5° C. on a heated water bath and stir the mixture to disperse the mixture completely.

In a second step, weight and mix specified amounts of capsaicin extract, lidocaine, stearic acid, cetyl alcohol, isopropyl palmitate, propyl paraben, *Piper nigrum* (black pepper) oil, *Curcuma longa* (tumeric) oil, *Cannabis sativa* (hemp) oil and sorbitan monostearate separately in a suitable glass container and heat to 80±5° C. on a heated water bath. Stir the dispersion to mix all components.

In a third step, mix the components of step-II with the components of step-I at 80±5° C. under continuous homogenization for 10-15 minutes.

In a fourth step, remove the mixture from the heated water bath, add specified amount of menthol, camphor, natural saffron yellow color formula 3635C and flavoring agent (bergamot mint oil) and homogenize continuously to disperse them uniformly.

In a fifth step, add the cream base.

In a sixth step, when the temperature of the composition is just above the solidification, the formulation is poured in to the suitable well labeled aluminum tubes. The final product is cooled down to room temperature, capped and stored at room temperature.

FIG. 1 shows the main ingredients 100 of a topical composition for pain relief used in an embodiment containing methyl salicylate. FIG. 2 shows the main ingredients 200 of a topical composition for pain relief used in an embodiment where hemp oil and cap saicin extract are used in place of methyl salicylate. FIG. 3 shows the purpose 300 of each of the topical composition for pain relief ingredients.

Experimental Results

It has been found that the composition can be used to treat generalized muscle and joint pain and inflammation. For example, the composition can be used: as a topical anti-inflammatory to treat localize inflammation; as a moisturizer and conditioner for the skin as a secondary effect when used for the purpose of reducing pain or inflammation as described above; in conjunction with other systemic anti-inflammatories as in a gouty attack, resulting in significant reduction in pain and inflammation. Localized pain relief is provided for up to 4 to 6 hours.

Recommendations for Use

Pregnancy: Use not recommended in pregnancy. Consult with your Physician prior to use.

Interactions: Consult with your Physician if on blood thinners, have kidney, liver or heart disease, and/or suffer from high blood pressure. Use only under the explicit guidance and approval of a physician if any of the above conditions exist. Allergy: Do not use this product if allergic to aspirin or to any of the active or inactive ingredients listed on the package.

Caution: Do not use with alcohol or any other topical medication. Consult a physician or a pharmacist for possible cross-reactions or interactions when taking or using other medications. Long-term use is not recommended. Chronic use beyond 7 days should be done under the supervision/guidance of a physician.

Application

For use, the composition is typically rubbed onto the skin in the areas of pain and/or inflammation, two or three times daily. Apply the cream to a small section of the affected area prior to more generalized use. Immediately stop using the cream and notify your Physician in the event of any allergic or hypersensitivity reaction. If an allergic reaction such as a rash, hives or a more severe reaction occurs, consult a medical professional immediately or call 911 should the reaction appear to be life threatening.

What follows is a random selection of exemplary results. Pain levels are recorded based on a scale of 1-3 low pain, 4-6 moderate pain, and 7-10 severe pain. Inflammation levels are recorded based on a scale of 1 for no reduction in swelling to 10 for a profound reduction in swelling. Patients 1 and 2 were treated with the first embodiment of the topical composition for pain relief. Other patients were treated with the second embodiment of the topical composition for pain relief.

Patient 1: An adult male complained of chronic back pain. A severe pain baseline of 7 was determined before use of the topical composition for pain relief. Inflammatory response was not measured. After use of the cream, a moderate pain level of 4 was determined. No adverse side effects were observed.

Patient 2: An adult male complained of a right ankle bone bruise. A moderate pain baseline of 5 was determined before use of the topical composition for pain relief. After use of the cream, a low pain level of 1 was determined along with an inflammation response of 3. No adverse side effects were observed.

Patient 3: An adult male complained of a wrist sprain. A moderate pain baseline of 6 was determined before use of the topical composition for pain relief. After use of the cream, a low pain level of 1 was determined along with an inflammation response of 3. No adverse side effects were observed.

Patient 4: An adult male complained of Achilles tendonitis. A moderate pain baseline of 5 was determined before use of the topical composition for pain relief. After 3 days of use, applying the cream twice a day, a low pain level of 1 was determined along with an inflammation response of 9. No side effects were observed.

Patient 5: An adult male complained of arthritis following knee surgery and removal of a majority of the medial meniscus. A moderate pain baseline of 4 was determined before the use of the topical composition for pain relief. After three applications of the cream over a two day period, the discomfort essentially disappeared and a pain level of 1 was determined along with an inflammation response of 5. Side effect was noticeable smell of cream during first hour after application.

While various embodiments of the present invention have been described above, it should be understood that they have been presented by way of example only, and not limitation. It will be apparent to those skilled in the art that various changes in the form and details can be made without departing from the spirit and scope of the invention. As such, the breadth and scope of the present invention should not be limited by the above-described exemplary embodiments, but should be defined only in accordance with the following claims and equivalents thereof.

What is claimed is:

1. A pain relief amount of a composition consisting essentially of therapeutically effective amounts of methyl salicylate, methyl sulfonyl methane, *arnica montana*, camphor, harpagophytim tincture, lidocaine, and maqui.

* * * * *